(12) United States Patent
Lee et al.

(10) Patent No.: US 10,926,262 B2
(45) Date of Patent: Feb. 23, 2021

(54) BIOCHIP PILLAR STRUCTURE

(71) Applicant: MBD CO., LTD., Suwon-si (KR)

(72) Inventors: Don Jung Lee, Yongin-si (KR); Ho Jeong Song, Suwon-si (KR); Dong Woo Lee, Suwon-si (KR)

(73) Assignee: MBD CO., LTD., Suwon-si (KR)

( * ) Notice: Subject to any disclaimer, the term of this patent is extended or adjusted under 35 U.S.C. 154(b) by 304 days.

(21) Appl. No.: 15/779,452

(22) PCT Filed: Dec. 12, 2016

(86) PCT No.: PCT/KR2016/014501
§ 371 (c)(1),
(2) Date: May 25, 2018

(87) PCT Pub. No.: WO2017/099545
PCT Pub. Date: Jun. 15, 2017

(65) Prior Publication Data
US 2018/0333718 A1    Nov. 22, 2018

(30) Foreign Application Priority Data

Dec. 11, 2015 (KR) .......................... 10-2015-0177110

(51) Int. Cl.
*B01L 3/00* (2006.01)
*G01N 33/50* (2006.01)
(Continued)

(52) U.S. Cl.
CPC .......... *B01L 3/5085* (2013.01); *B01J 19/0046* (2013.01); *B01L 3/5088* (2013.01);
(Continued)

(58) Field of Classification Search
CPC . C12Q 1/02; C12Q 1/24; G01N 33/48; G01N 33/53; G01N 33/50; B01L 3/00;
(Continued)

(56) References Cited

U.S. PATENT DOCUMENTS

| | | | |
|---|---|---|---|
| 6,110,247 A * | 8/2000 | Birmingham | B01D 45/08 55/442 |
| 10,379,107 B2 * | 8/2019 | Gobaa | B01J 19/0046 |

(Continued)

FOREIGN PATENT DOCUMENTS

| | | |
|---|---|---|
| KR | 10-2012-0026999 A | 3/2012 |
| KR | 10-2012-0044650 A | 5/2012 |

(Continued)

*Primary Examiner* — Benjamin R Whatley
*Assistant Examiner* — Curtis A Thompson
(74) *Attorney, Agent, or Firm* — Novick, Kim & Lee, PLLC; Sang Ho Lee (57) ABSTRACT

Technology for a biochip pillar structure is disclosed. According to an embodiment of the present disclosure, the biochip pillar structure includes: a pillar structure including a plate-shaped first substrate portion, and pillar portions protruding from a surface of the first substrate portion; and a well structure including a plate-shaped second substrate portion, and well portions formed in a surface of the second substrate portion and having a predetermined depth to respectively receive the pillar portions of the pillar structure, wherein the well portions have a diameter within a range of 800 μm to 1500 μm, and the pillar portions configured to be inserted into the well portions have a diameter of which the ratio to the diameter of the well portions ranges from 0.3 to 0.58, thereby providing a high-density biochip and preventing bubbling in an aqueous liquid contained in the well portions when the pillar portions are inserted.

2 Claims, 8 Drawing Sheets

(51) Int. Cl.
*B01J 19/00* (2006.01)
*C40B 60/12* (2006.01)

(52) U.S. Cl.
CPC ....... *G01N 33/50* (2013.01); *B01J 2219/0047* (2013.01); *B01J 2219/00387* (2013.01); *B01J 2219/00509* (2013.01); *B01L 2200/021* (2013.01); *B01L 2200/025* (2013.01); *B01L 2200/0684* (2013.01); *B01L 2300/0819* (2013.01); *B01L 2300/0832* (2013.01); *B01L 2300/0848* (2013.01); *C40B 60/12* (2013.01)

(58) Field of Classification Search
CPC .......... C12M 1/32; C40B 40/00; C40B 40/02; C40B 50/06
See application file for complete search history.

(56) References Cited

U.S. PATENT DOCUMENTS

| | | | | |
|---|---|---|---|---|
| 2012/0088693 A1* | 4/2012 | Lee | ........................ | C12M 23/12 506/15 |
| 2012/0165224 A1* | 6/2012 | Song | ........................ | C40B 60/12 506/13 |
| 2012/0309649 A1* | 12/2012 | Lee | ........................ | C40B 60/12 506/14 |
| 2013/0101480 A1* | 4/2013 | Yang | ........................ | B01L 3/5088 422/552 |
| 2013/0184182 A1* | 7/2013 | Lee | ........................ | B01L 3/5088 506/13 |
| 2014/0011711 A1 | 1/2014 | Lee et al. | | |
| 2014/0134652 A1* | 5/2014 | Honkanen | ........................ | B01L 3/50853 435/7.92 |

FOREIGN PATENT DOCUMENTS

| | | | | |
|---|---|---|---|---|
| KR | 10-2012-0071216 A | 7/2012 | | |
| KR | 20120044650 | * 7/2012 | ............... | C12Q 1/02 |
| KR | 10-2012-0132999 A | 12/2012 | | |
| KR | 10-1218986 B1 | 1/2013 | | |
| KR | 10-2013-0084394 A | 7/2013 | | |
| WO | 93/09872 A | 5/1993 | | |
| WO | WO-9309872 A1 * | 5/1993 | ....... | G01N 33/54366 |
| WO | WO-2013037836 A1 * | 3/2013 | ............... | G03F 7/20 |

* cited by examiner

BIOCHIP PILLAR STRUCTURE

TECHNICAL FIELD

The present disclosure relates to a biochip pillar structure, and more particularly, to a biochip pillar structure enabling the implementation of a high-density biochip and preventing the formation of bubbles in an aqueous liquid contained in well portions when pillar portions are inserted into the well portions.

BACKGROUND ART

In general, biochips refer to microchips used to analyze genetic defects, protein distribution, reaction behaviors, or the like by placing biological micro-object samples such as DNA, proteins, or cells on small substrates.

Such a biochip includes: a pillar structure having a substrate portion and a plurality of micro pillar portions formed on the substrate portion; and a well structure having a substrate portion and a plurality of well portions formed in the substrate portion. When conducting an experiment using the biochip, it is necessary to secure a large experimental space on the biochip to obtain more accurate and reliable experimental results and increase the efficiency of the experiment. That is, when manufacturing a biochip, it is necessary to impart high density to the biochip by forming as many well portions and pillar portions corresponding to the well portions as possible per unit area.

However, in the related art as disclosed in Korean Patent Application Publication No. 10-2013-0084394 and Korean Patent Publication No. 10-1218986, a sample is placed on pillar portions having a simple cylindrical shape, and the pillar portions are inserted into well portions having a cylindrical hole shape. Thus, if the diameter of the well portions is decreased for increase the density of a biochip, bubbling occurs in an aqueous liquid contained in the well portions. That is, if the diameter of the well portions is decreased, gaps between sidewalls of the well portions and the pillar portions are reduced, and thus when the pillar portions are inserted, air contained in the well portions and not yet discharged from the well portions forms bubbles in the aqueous liquid contained in the well portions. If bubbles are formed in the aqueous liquid as described above, the sample immersed in the aqueous liquid may wither or be damaged.

On the other hand, if the diameter of the pillar portions is excessively decreased to increase the gaps between the sidewalls of the well portions and the pillar portions, the amount of the sample that can be placed on distal end surfaces of the pillar portions is limited, thereby making it difficult to effectively conduct experiments and easily causing separation or damage of the sample when external force or vibration is applied to the biochip because of a decreased sample attachment area.

DESCRIPTION OF EMBODIMENTS

Technical Problem

Provided is a biochip pillar structure enabling the implementation of a high-density biochip, preventing the formation of bubbles in an aqueous liquid contained in well portions when pillar portions are inserted into the well portions, and preventing separation or damage of a sample caused by external force or vibration.

Solution to Problem

According to an aspect of the present disclosure, a biochip pillar structure includes: a pillar structure including a first substrate portion having a plate shape, and a plurality of pillar portions protruding from a surface of the first substrate portion; and a well structure including a second substrate portion having a plate shape, and a plurality of well portions formed in a surface of the second substrate portion and having a predetermined depth to respectively receive the plurality of pillar portions of the pillar structure, wherein the plurality of well portions have a diameter within a range of 800 μm to 1500 μm, and the pillar portions configured to be inserted into the well portions have a diameter having a ratio to the diameter of the well portions of 0.3 to 0.58.

In an embodiment, the pillar structure may include stepped portions between the first substrate portion and the pillar portions, and the stepped portions may have a diameter greater than the diameter of the pillar portions and less than the diameter of the well portions.

In an embodiment, the stepped portions may include air discharge grooves configured to induce discharge of air from insides of the well portions when the pillar portions and the stepped portions are inserted into the well portions.

Advantageous Effects of Disclosure

According to the present disclosure, the diameter ratio of the pillar portions and the well portions of a biochip are optimized, thereby imparting high density to the biochip and preventing the formation of bubbles in an aqueous liquid of the well portions when the pillar portions are inserted into the well portions.

In addition, the stepped portions having a diameter greater than the diameter of the pillar portions but less than the diameter of the well portions of the well structure are provided between the substrate portion and the pillar portions of the pillar structure, thereby decreasing collision impact between the sidewalls of the well portions and the pillar portions caused by external force or vibration and preventing separation or damage of a sample placed on the pillar portions while preventing formation of bubbles in an aqueous solution contained in the well portions.

In addition, owing to the air discharge grooves formed in the stepped portions, rapid discharge of air from the inside of the well portions may be induced when the pillar portions and the stepped portions are inserted into the well portions.

In addition, those of ordinary skill in the art will clearly understand from the following description that various embodiments of the present disclosure may also be useful to solve various technical problems not mentioned above.

BEST MODE

Hereinafter, embodiments of the present disclosure will be described in detail with reference to the accompanying drawings so that methods for solving technical problems of the present disclosure may be clearly understood. However, detailed descriptions relating to well-known techniques may be omitted in order not to unnecessarily obscure subject matters of the present disclosure. In addition, terms used herein are defined in consideration of functions of the present disclosure, but the terms may vary according to the intention of designer or manufactures, precedents, or the like. Therefore, these terms should be construed based on the entirety of the present disclosure.

Figure 1:
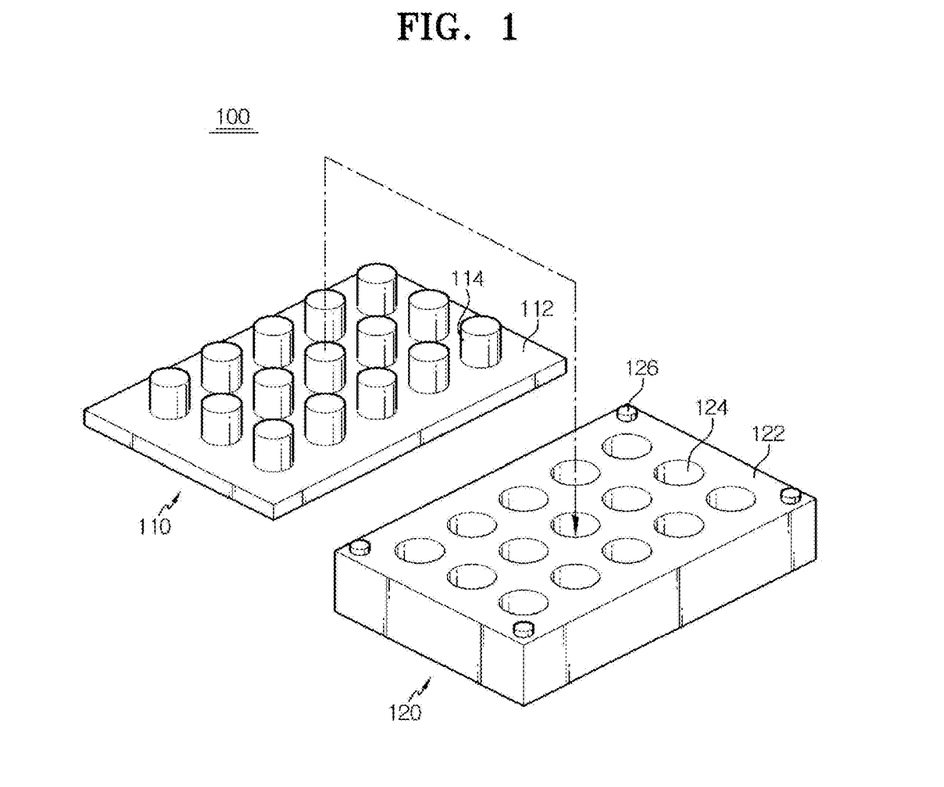
FIG. 1 is a view illustrating an example of a biochip according to the present disclosure.

FIG. 1 is a view illustrating an example of a biochip 100 according to the present disclosure.

As illustrated in FIG. 1, the biochip 100 includes a pillar structure 110 and a well structure 120. In general, the pillar structure 110 has a structure in which a plurality of micro pillar portions 114 are formed on a surface of a plate-shaped substrate portion 112. A sample including biological micro-objects such as DNA, proteins, or cells is placed on each of distal ends of the pillar portions 114. The well structure 120 has a structure in which a plurality of micro well portions 124 configured to receive the pillar portions 114 of the pillar structure 110 are formed in a surface of a plate-shaped substrate portion 122. A certain amount of a liquid such as a culture medium or a reagent is ejected and accommodated in each of the well portions 124. The pillar structure 110 is coupled to the well structure 120, and then the sample placed on the pillar portions 114 is placed in an aqueous solution inside the well portions 124. In addition, the well structure 120 may include spacer members 126. The spacer members 126 are placed between coupling surfaces of the pillar structure 110 and the well structure 120 to prevent the well portions 124 from being hermetically sealed when the pillar structure 110 and the well structure 120 are coupled to each other.

Figure 2:
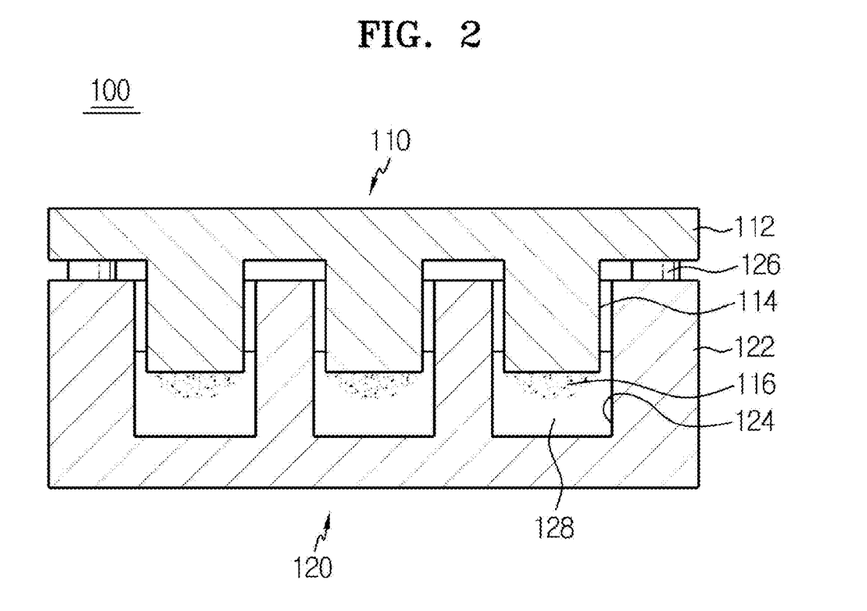
FIG. 2 is a vertical cross-sectional view illustrating an example state in which a pillar structure and a well structure are coupled to each other.

FIG. 2 is a vertical cross-sectional view illustrating an example state in which the pillar structure 110 and the well structure 120 are coupled to each other.

As illustrating in FIG. 2, when the pillar structure 110 and the well structure 120 are coupled to each other, each of the pillar portions 114 is inserted into a corresponding one of the well portions 124, and a sample 116 placed on the pillar portions 114 is immersed in an aqueous liquid 128 contained in the well portions 124. After a certain period of time, in a state in which the pillar structure 110 is coupled to or separated from the well structure 120, an experimenter may observe and analyze the state of the sample 116 placed on the pillar portions 114 of the pillar structure 110 using a fluorescence microscope or the like. To this end, the pillar structure 110 is formed of a resin composition having high light transmittance. For example, the pillar structure 110 may be formed of a resin composition material including polystyrene, maleic anhydride, or the like. In addition, when the pillar structure 110 is actually manufactured, the resin composition material is melted, injection-molded, and cooled according to an injection molding method.

Figure 3:
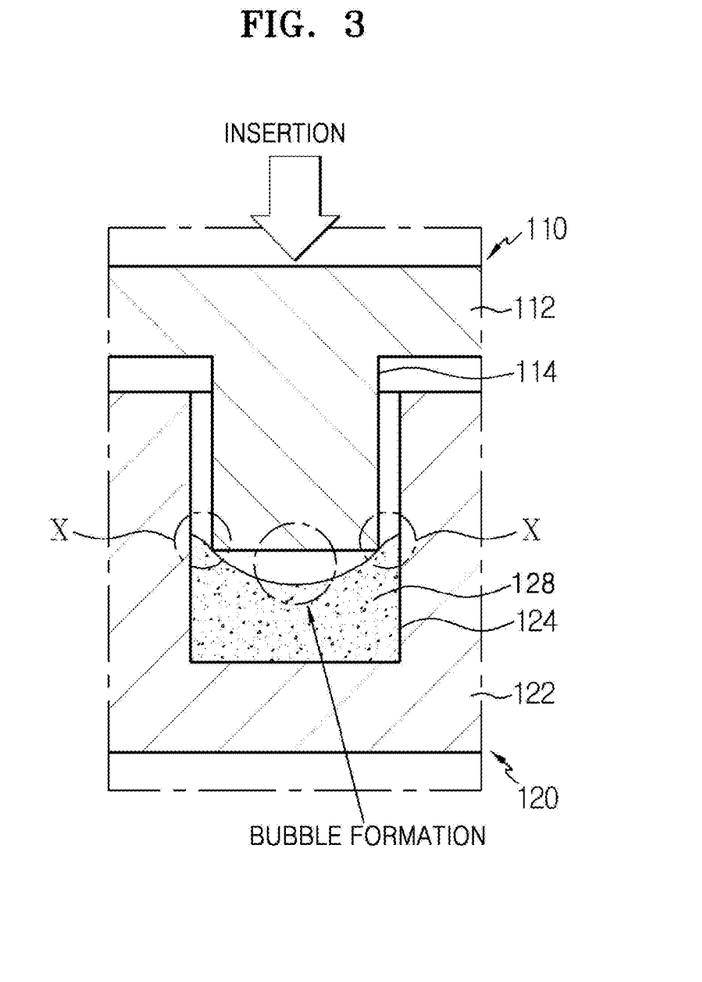
FIG. 3 is a view illustrating a structural cause of bubble formation in a well portion.

FIG. 3 illustrates a structural cause of bubble formation in the well portions 124.

As illustrated in FIG. 3, when the diameter of the well portions 124 of the well structure 120 is reduced for implementing a high-density biochip, or the diameter of the pillar portions 114 of the pillar structure 110 is increased for easy distribution of a sample, gaps between sidewalls of the well portions 124 and the pillar portions 114 are reduced. In addition, the surface of the aqueous liquid 128 contained in the well portions 124 is higher at edge portions X than center portions because of surface tension. In general, since the diameter of the well portions 124 is small at about 100 μm to about 6000 μm, when the pillar portions 114 are inserted into the well portions 124, the edge portions X are first brought into contact with the pillar portions 114, and thus air existing on the surfaces of the center portions of the aqueous liquid 128 may not escape but may be immersed in the aqueous liquid 128 together with the pillar portions 114, thereby forming bubbles. In addition, when the aqueous liquid 128 is discharged from the well portions 124, or the pillar portions 114 are repeatedly inserted into and separated from the well portions 124, some of the aqueous liquid 128 may cling to the sidewalls of the well portions 124 and form bubbles when the pillar portions 114 are inserted. As described above, if bubbles are formed in an aqueous liquid such as a culture solution contained in a well portion, a sample such as cells that has to be supplied with substances necessary for survival will be exposed to air and thus will wither or be damaged.

Figure 4A:
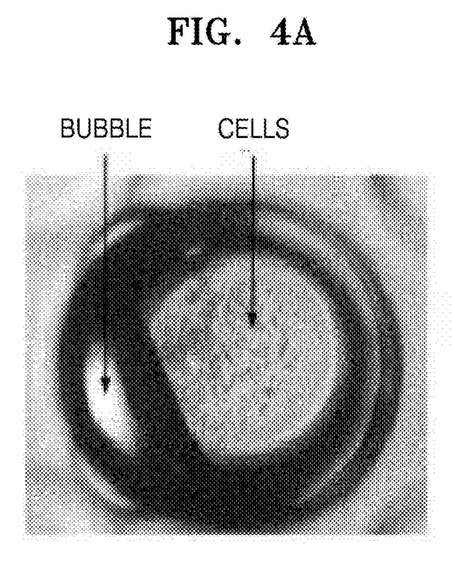
FIGS. 4A and 4B are images illustrating the inside of a well portion in which a bubble is formed and the state of a sample after an experiment.
Figure 4B:
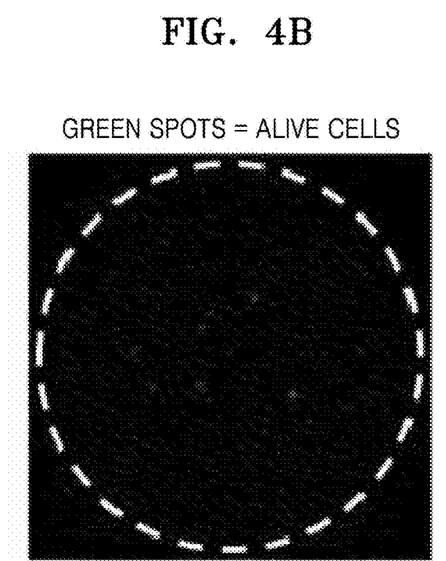

FIGS. 4A and 4B are images showing the inside of a well portion in which a bubble is formed and the state of a sample after an experiment. FIG. 4A is an optical microscope image showing the inside of a well portion, and FIG. 4B is an image showing cells colored to check whether the cells are alive after the experiment. The cells were colored with green.

As shown in FIG. 4A, if the gaps between the pillar portions 114 and the well portions 124 are narrow when the pillar portions 114 are inserted, bubbles are formed in a culture solution contained in the well portions 124 (refer to a left portion of FIG. 4A). Therefore, although a sufficient amount of cells are placed on the pillar portions 114, since the cells requiring supply of substances necessary for survival from the culture solution are exposed to air, the cells may not grow but wither or be damaged with time. As a result, as shown in FIG. 4B, when the cells placed on the pillar portions 114 are colored to observe whether the cells are alive, there will be almost no alive cell. In FIG. 4B, very few green spots within a dashed-line circle indicate alive cells.

Therefore, according to the present disclosure, the diameter ratio of the pillar portions 114 and the well portions 124 of a biochip pillar structure are optimized, thereby imparting high density to the biochip pillar structure and preventing the formation of bubbles in an aqueous liquid contained in the well portions when the pillar portions are inserted.

Figure 5:
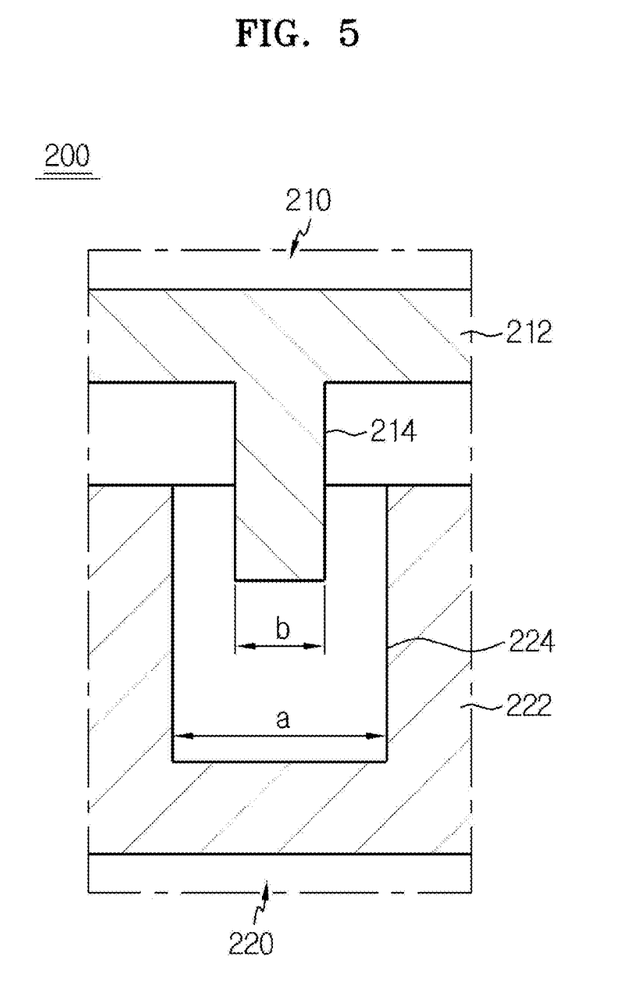
FIG. 5 is a partial cross-sectional view illustrating a biochip pillar structure according to an embodiment of the present disclosure.

FIG. 5 is a partial cross-sectional view illustrating a biochip pillar structure 200 according to an embodiment of the present disclosure.

As illustrated in FIG. 5, according to the embodiment of the present disclosure, the biochip pillar structure 200 includes a pillar structure 210 and a well structure 220.

First, the pillar structure 210 includes a first substrate portion 212 and a pillar portion 214. The first substrate portion 212 forms a base of the pillar structure 210 and has a plate shape. The pillar portion 214 protrudes from a surface of the first substrate portion 212. A plurality of such pillar portions 214 are formed. When the pillar structure 210 and the well structure 220 are coupled to each other, the pillar portions 214 are inserted into well portions 224 of the well structure 220. A sample is placed on distal ends of the pillar portions 214. A dispersion material layer (not shown) may be applied to the distal ends of the pillar portions 214 for easy placement of the sample. The dispersion material layer is formed of a porous material permeable to an aqueous liquid such as a culture solution or a reagent contained in the well portions 224. For example, the dispersion material layer may include a material such as sol-gel, hydrogel, alginate gel, organogel, xerogel, or collagen. In this case, the sample is placed by dispersing the sample in the dispersion material layer.

The well structure 220 includes a second substrate portion 222 and the well portions 224. The second substrate portion 222 forms a base of the well structure 220 and has a plate shape. The well portions 224 are formed in a surface of the second substrate portion 222 and have a predetermined depth. The well portions 224, formed at a plurality of positions in the surface of the second substrate portion 222, correspond to the pillar portions 214 of the pillar structure 210. In general, the well portions 224 may have a depth of 1000 μm, and a manufacturer or the like may properly determine the depth of the well portions 224 according to the subject or conditions of experiment.

The well portions 224 may have a diameter (a) in a wide range. In the present disclosure, the well portions 224 have a diameter (a) within the range of 800 μm to 1500 μm. That is, if the diameter (a) of the well portions 224 is greater than 1500 μm, it is difficult to provide a high-density biochip, and the efficiency of experiment is low. In addition, if the diameter (a) of the well portions 224 is less than 800 μm, the diameter of the pillar portions 214 of the pillar structure 210 is accordingly small. Thus, it is difficult to place a sample on the pillar portions 214, and the amount of a sample placed on the pillar portions 214 is excessively small. However, when the diameter (a) of the well portions 224 ranges from 800 μm to 1500 μm, it is possible to provide a biochip having a significantly high density guaranteeing accurate and reliable experimental results and versatility for application to various samples while maintaining the efficiency of biochip manufacturing processes and ease of experiments with the biochip.

In this case, particularly, the pillar portions 214 to be inserted into the well portions 224 have a diameter (b) of which the ratio b/a to the diameter (a) of the pillar portions 214 is within the range of 0.3 to 0.58. That is, the ratio b/a of the diameter (b) of the pillar portions 214 to the diameter (a) of the well portions 224 has a threshold of 0.58. If the ratio b/a is greater than the threshold, when the pillar portions 214 are inserted, the probability of bubbling in the well portions 224 markedly increases, and thus the number of well portions of the biochip in which bubbles are formed markedly increases. In addition, if the ratio b/a of the diameter (b) of the pillar portions 214 to the diameter (a) of the well portions 224 is less than 0.3, the pillar portions 214 have an excessively small sample placement area, making it difficult to place a sample and excessively decreasing the amount of a sample that can be placed on the pillar portions 214. However, if the ratio b/a of the diameter (b) of the pillar portions 214 to the diameter (a) of the well portions 224 is within the range of 0.3 to 0.58, it may be easy to place a sample, and the formation of bubbles in an aqueous liquid contained in the well portions 224 may be fundamentally prevented when the pillar portions 214 are inserted into the pillar portions 214.

Figure 6:
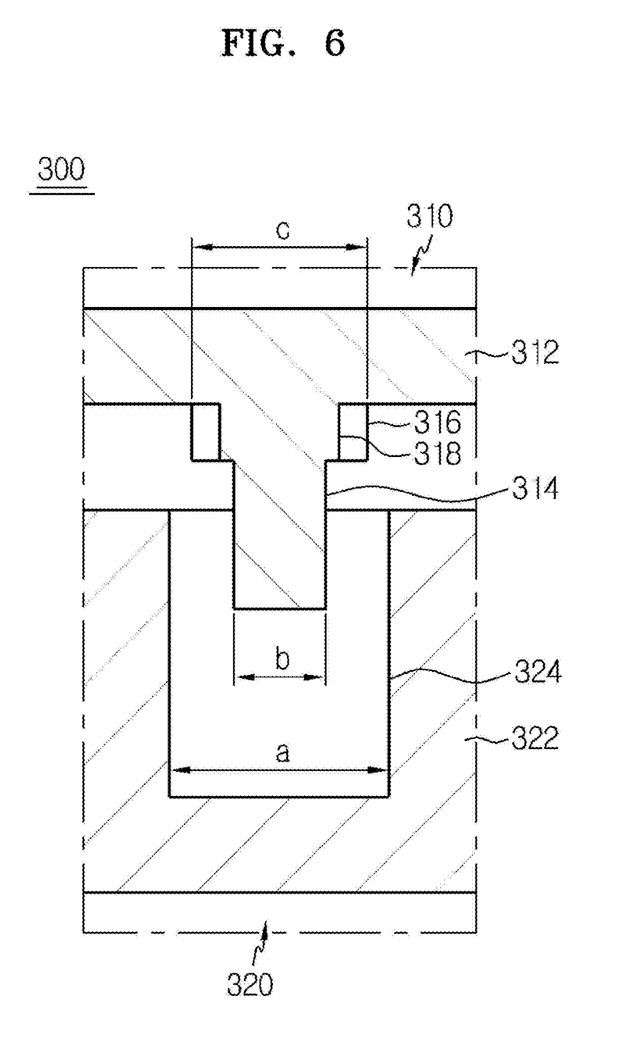
FIG. 6 is a partial cross-sectional view illustrating a biochip pillar structure according to another embodiment of the present disclosure.

FIG. 6 is a partial cross-sectional view illustrating a biochip pillar structure 300 according to another embodiment of the present disclosure.

As illustrated in FIG. 6, according to the other embodiment of the present disclosure, the biochip pillar structure 300 includes a pillar structure 310 and a well structure 320. The pillar structure 310, a first substrate portion 312 and pillar portions 314 forming the pillar structure 310, the well structure 320, and a second substrate portion 322 and well portions 324 forming the well structure 320 are the same as those described with reference to FIG. 5. In addition, the well portions 324 of the well structure 320 have a diameter (a) within the range of 800 μm to 1500 μm. In addition, the pillar portions 314 of the pillar structure 310 to be inserted into the well portions 324 have a diameter (b) of which the ratio b/a to the diameter (a) of the well portions 324 is within the range of 0.3 to 0.58.

Particularly, the pillar structure 310 includes a stepped portion 316 between the first substrate portion 312 and each of the pillar portions 314. The stepped portion 316 may have a diameter (c) which is greater than the diameter (b) of the pillar portions 314 but less than the diameter of the well portions 324.

Figure 7:
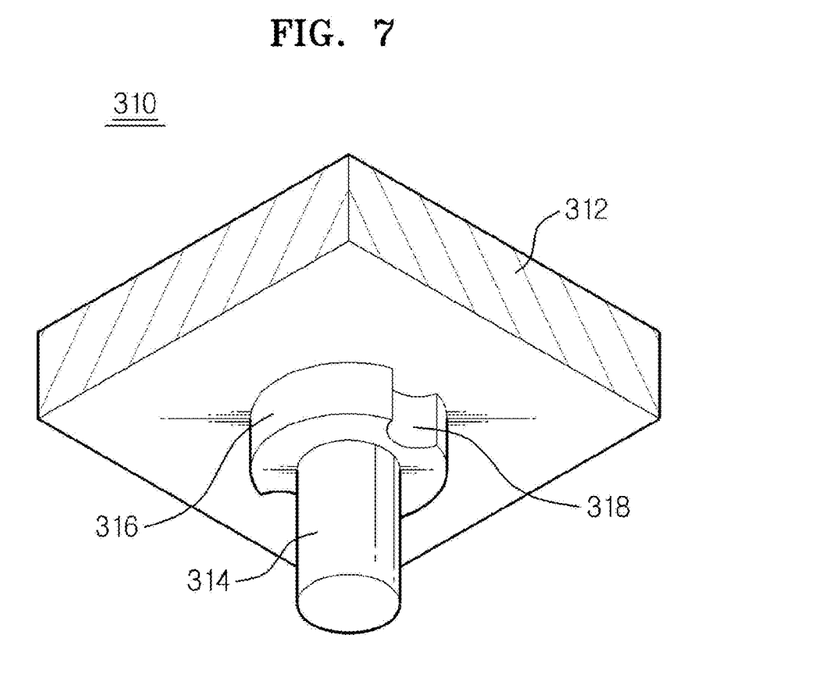
FIG. 7 is a perspective view illustrating a pillar structure illustrated in FIG. 6.
Figure 8:
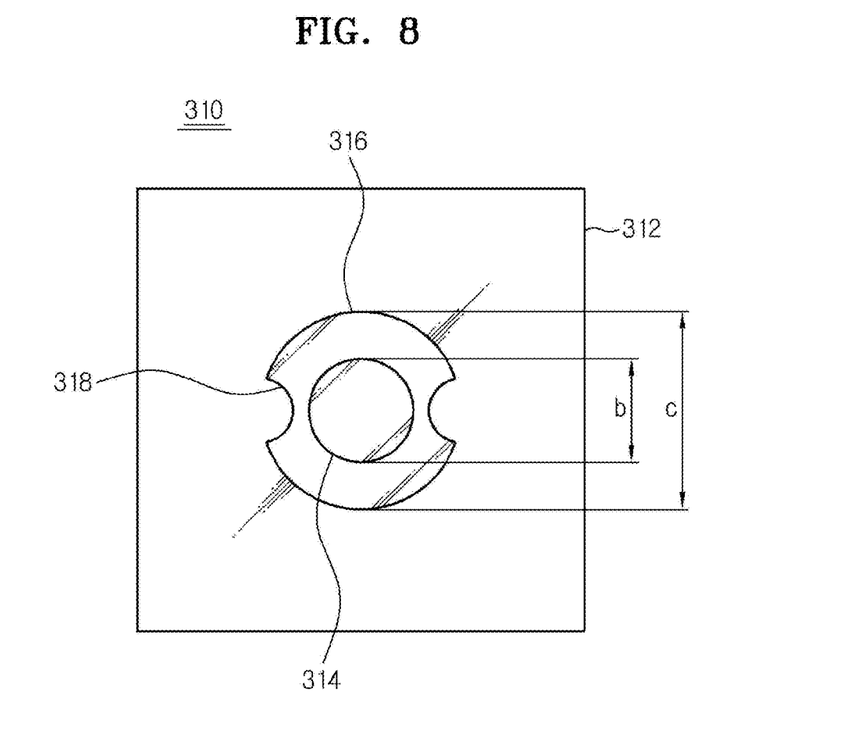
FIG. 8 is a bottom view illustrating the pillar structure illustrated in FIG. 6.

FIG. 7 is a perspective view illustrating the pillar structure 310 shown in FIG. 6, and FIG. 8 is a bottom view illustrating the pillar structure 310 shown in FIG. 6.

As illustrated in FIGS. 7 and 8, the stepped portion 316 of the pillar structure 310 is located between the first substrate portion 312 and each of the pillar portions 314 of the pillar structure 310 to form a height difference with the pillar portion 314. That is, the stepped portion 316 has a diameter (c) which is greater than the diameter (b) of the pillar portions 314 but less than the diameter of the well portions 324. In this case, the diameter (c) of the stepped portion 316 may be similar to the diameter (a) of the well portion 224. As described above, according to the present disclosure, the diameter ratio b/a of the pillar portions 314 and the well portions 324 is optimized to prevent bubbling in an aqueous liquid contaned in the well portions 324, and at the same time the stepped portions 316 may decrease collision impact between sidewalls of the well portions 324 and the pillar portions 314 that perhaps occurs due to a reduced diameter of the pillar portions 314 and may prevent separation or damage of a sample placed on the pillar portions 314.

In addition, the stepped portions 316 may include air discharge grooves 318. The air discharge grooves 318 are formed to induce rapid discharge of air from the inside of the well portions 324 when the pillar portions 314 and the stepped portions 316 are inserted into the well portions 324. As described above, according to the present disclosure, the stepped portions 316 decrease collision impact between the sidewalls of the well portions 324 and the pillar portions 314, and along with this, the air discharge grooves 318 formed in the stepped portions 316 make it easy to couple the pillar structure 310 and the well structure 320 to each other.

In the present disclosure, it has been described that the pillar portions, the well portions, and the stepped portions of the biochip pillar structure have circular horizontal cross-sections. However, the horizontal cross-sections of the pillar portions, the well portions, and the stepped portions of the biochip pillar structure may have other shapes such as a polygonal shape than the circular shape. When the pillar portions, the well portions, and the stepped portions have horizontal cross-sections such as polygonal horizontal cross-sections, the diameters of the pillar portions, the well portions, and the stepped portions refer to widths of the horizontal cross-sections.

Figure 9:
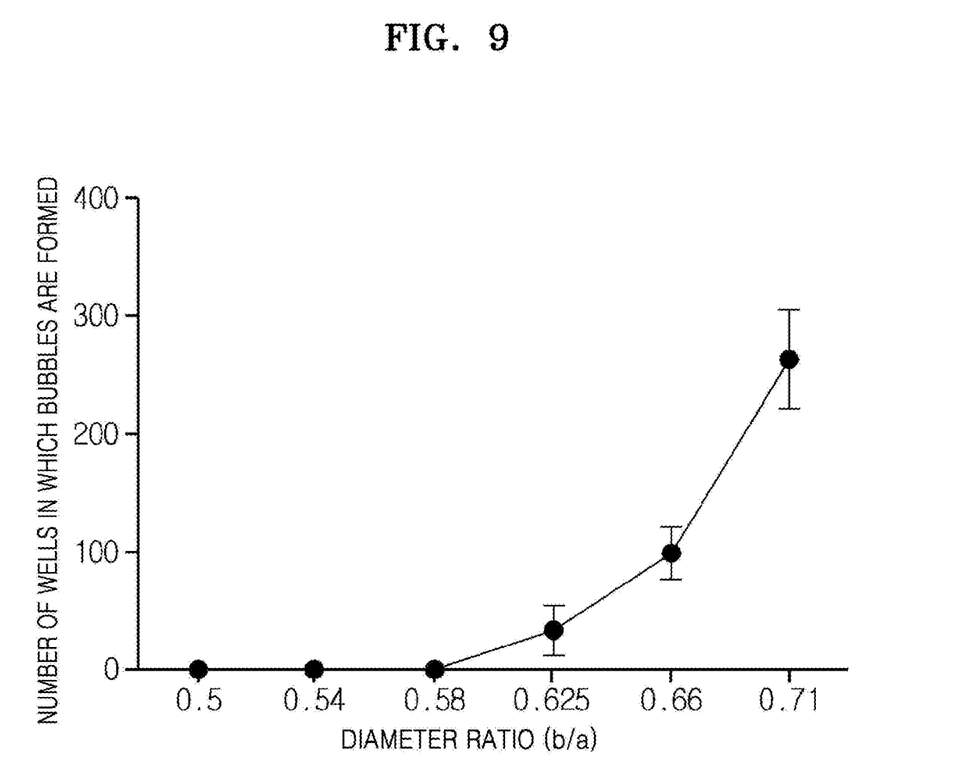
FIG. 9 is a graph illustrating results of an experiment in which the number of well portions experiencing bubbling was observed according to the diameter ratio of a pillar portion to a well portion.

FIG. 9 is a graph showing results of an experiment in which the number of well portions experiencing bubbling was observed according to the diameter ratio of pillar portions and well portions. Table 1 below shows numerical data of the results of the experiment. In the experiment, a biochip having 532 pillar portions and 532 well portions was used, 950 nl of a culture solution was injected into each of the well portions having a diameter (a) of 1200 μm at room temperature, and insertion and separation of the pillar portions into and from the well portions were repeated 20 times during 2 minutes.

TABLE 1

| Well diameter [μm] (a) | Pillar diameter [μm] (b) | Diameter ratio (b/a) | Number of wells in which bubbling occurs | | | | |
|---|---|---|---|---|---|---|---|
| | | | First Experiment | Second Experiment | Third Experiment | Average | Standard deviation |
| 1200 | 600 | 0.5 | 0 | 0 | 0 | 0 | 0 |
| 1200 | 650 | 0.54 | 0 | 0 | 0 | 0 | 0 |
| 1200 | 700 | 0.58 | 1 | 0 | 3 | 1.333333 | 1.527525 |
| 1200 | 750 | 0.625 | 10 | 54 | 34 | 32.66667 | 22.03028 |
| 1200 | 800 | 0.66 | 78 | 124 | 92 | 98 | 23.57965 |
| 1200 | 850 | 0.71 | 310 | 230 | 250 | 263.3333 | 41.63332 |

As shown in FIG. 9 and Table 1, when the ratio b/a of the diameter (b) of the pillar portions to the diameter (a) of the well portions is less than the threshold of 0.58, although the pillar portions were repeatedly inserted into and separated from the well portions, bubbling did not occur in all the well portions of the biochip. However, when the ratio b/a of the diameter (b) of the pillar portions to the diameter (a) of the well portions is greater than 0.58, the probability of bubbling in the well portions markedly increased when the pillar portions were inserted, and the number of well portions of the biochip in which bubbling occurred was steeply increased.

Figure 10A:
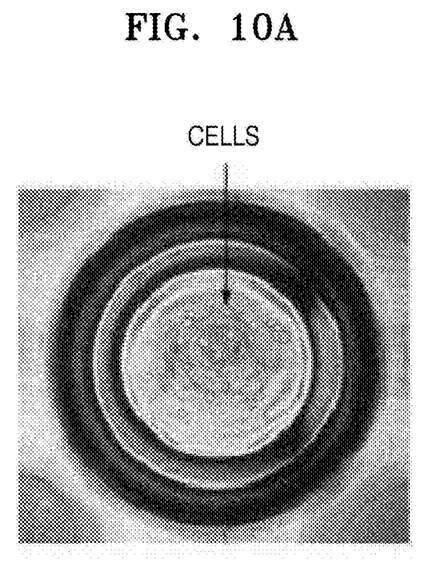
FIGS. 10A and 10B are images illustrating the inside of a well portion of a biochip pillar structure of the present disclosure, and the state of a sample after an experiment.
Figure 10B:
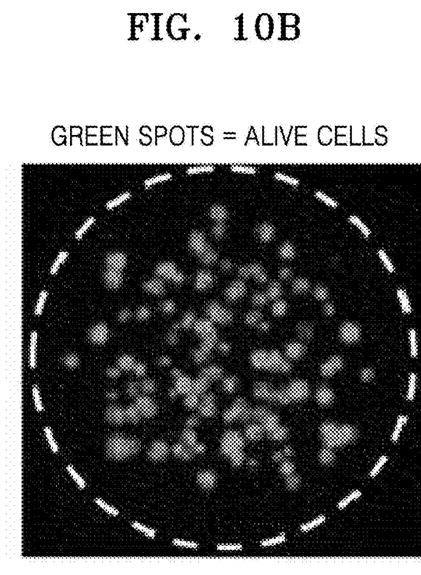

FIGS. 10A and 10B are images showing the inside of a well portion of a biochip pillar structure of the present disclosure, and the state of a sample after an experiment. FIG. 10A is an optical microscope image showing the inside of the well portion of the biochip pillar structure of the present disclosure, and FIG. 10B is an image showing cells colored to check whether the cells are alive after the experiment. The cells were colored with green.

As illustrated in FIG. 10A, in the biochip pillar structure of the present disclosure, even when a pillar portion was inserted into the well portion, no bubble was formed in a culture solution contained in the well portion unlike the case shown in FIG. 4A. In addition, as illustrated in FIG. 10B, in the biochip pillar structure of the present disclosure, the cells placed on the pillar portion grew well and proliferated with time unlike the case shown in FIG. 4B. In FIG. 10B, many green spots within a dashed-line circle indicate alive cells.

As described above, according to the present disclosure, the diameter ratio of the pillar portions and the well portions of the biochip are optimized, thereby imparting high density to the biochip and preventing the formation of bubbles in an aqueous liquid contained in the well portions when the pillar portions are inserted. In addition, the stepped portions having a diameter greater than the diameter of the pillar portions but less than the diameter of the well portions of the well structure are provided between the substrate portion and the pillar portions of the pillar structure, thereby decreasing collision impact between the sidewalls of the well portions and the pillar portions caused by external force or vibration and preventing separation or damage of a sample placed on the pillar portions while preventing formation of bubbles in an aqueous liquid contained in the well portions. In addition, owing to the air discharge grooves formed in the stepped portions, rapid discharge of air from the inside of the well portions may be induced when the pillar portions and the stepped portions are inserted into the well portions. Furthermore, in relevant technical fields as well as in the technical field to which the present disclosure pertains, various embodiments of the present disclosure may be useful to solve various technical problems in addition to those problems mentioned in the present disclosure.

Specific embodiments of the present disclosure have been described. However, those of ordinary skill in the art will clearly understand that various modifications could be made within the scope of the present disclosure. Therefore, the embodiments described herein should be considered in a descriptive sense only and not for purposes of limitation. That is, the scope of the present disclosure should be defined by the following claims, and all differences within equivalents ranges of the scope of the present disclosure should be considered as being included in the scope of the present disclosure.

The invention claimed is:

1. A biochip structure comprising:
   a pillar structure comprising a first substrate portion having a plate shape, and a plurality of pillar portions protruding from a surface of the first substrate portion;
   a well structure comprising a second substrate portion having a plate shape, and a plurality of well portions formed in a surface of the second substrate portion and having a predetermined depth to respectively receive the plurality of pillar portions of the pillar structure; and
   a spacer member placed between coupling surfaces of the pillar structure and the well structure to prevent the well portions from being hermetically sealed when the pillar structure and the well structure are coupled to each other
   wherein the well structure further comprises a spacer member placed between coupling surfaces of the pillar structure and the well structure to prevent the well portions from being hermetically sealed when the pillar structure and the well structure are coupled to each other, wherein the plurality of well portions have a diameter within a range of 800 μm to 1500 μm, and the pillar portions configured to be inserted into the well portions have a diameter having a ratio to the diameter of the well portions of a range of 0.3 to 0.58, wherein the pillar structure further comprises stepped portions between the first substrate portion and the pillar portions, the stepped portions having a diameter greater than the diameter of the pillar portions and less than the diameter of the well portions, and wherein the stepped portions comprise air discharge grooves configured to induce discharge of air from insides of the well portions to facilitate coupling of the pillar structure and well structure and to prevent a formation of bubbles when the pillar portions and the stepped portions are inserted into the well portions.

2. The biochip structure of claim 1, wherein the air discharge grooves of the stepped portions form a semi-cylinder.

* * * * *